United States Patent
Cabrera (10) Patent No.: US 10,881,409 B2
(45) Date of Patent: Jan. 5, 2021

(54) ROTATION ASSEMBLY FOR A SURGICAL DEVICE

(71) Applicant: Covidien LP, Mansfield, MA (US)

(72) Inventor: Ramiro Cabrera, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 296 days.

(21) Appl. No.: 15/946,032

(22) Filed: Apr. 5, 2018

(65) Prior Publication Data

US 2018/0317921 A1    Nov. 8, 2018

Related U.S. Application Data

(60) Provisional application No. 62/500,116, filed on May 2, 2017.

(51) Int. Cl.
*A61B 17/115* (2006.01)
*A61B 17/068* (2006.01)
(Continued)

(52) U.S. Cl.
CPC ...... *A61B 17/1155* (2013.01); *A61B 17/0682* (2013.01); *A61B 17/072* (2013.01);
(Continued)

(58) Field of Classification Search
CPC .............. A61B 17/0682; A61B 17/072; A61B 17/1155; A61B 17/00234;
(Continued)

(56) References Cited

U.S. PATENT DOCUMENTS 3,193,165 A    7/1965   Akhalaya et al.
3,388,847 A    6/1968   Kasulin et al.
(Continued)

FOREIGN PATENT DOCUMENTS

CA    908529 A    8/1972
CA    2805365 A1  8/2013
(Continued)

OTHER PUBLICATIONS

European Search Report dated Sep. 11, 2018 issued in EP Appln. No. 18170232.

*Primary Examiner* — Thomas M Wittenschlaeger
(74) *Attorney, Agent, or Firm* — Carter, DeLuca & Farrell LLP (57) ABSTRACT

A surgical device includes an actuator assembly including a handle, an adapter assembly extending distally from the adapter assembly, and a tool assembly supported on a distal portion of the adapter assembly. The adapter assembly includes a rotation assembly that rotatably supports the adapter assembly in relation to the actuator assembly and a wire harness that allows the actuator assembly to communicate with the tool assembly. The rotation assembly includes a stop assembly for limiting a degree of rotation of the adapter assembly in relation to the actuator assembly to prevent separation of the wire harness from communication with the actuator assembly and/or the tool assembly. The stop assembly includes a stop plate and a stop pin that are spaced from the wire harness to minimize the likelihood of damage to the wire harness during rotation of the adapter assembly in relation to the actuator assembly.

20 Claims, 9 Drawing Sheets

(51) Int. Cl.
  *A61B 17/072* (2006.01)
  *A61B 17/00* (2006.01)
  *A61B 90/00* (2016.01)
  *A61B 17/29* (2006.01)
(52) U.S. Cl.
  CPC ............... *A61B 17/00234* (2013.01); *A61B 2017/00017* (2013.01); *A61B 2017/0046* (2013.01); *A61B 2017/00398* (2013.01); *A61B 2017/00477* (2013.01); *A61B 2017/00734* (2013.01); *A61B 2017/2904* (2013.01); *A61B 2017/2929* (2013.01); *A61B 2090/035* (2016.02); *A61B 2090/0814* (2016.02)
(58) Field of Classification Search
  CPC ...... A61B 2090/035; A61B 2090/0814; A61B 2017/2904; A61B 2017/2929; A61B 2017/00734; A61B 2017/00398; A61B 2017/00017; A61B 2017/0046; A61B 2017/00477
  See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A * | 3/1996 | Brady ............... A61B 17/072 227/176.1 |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A * | 11/1997 | Seeber ............... A61B 17/115 227/175.1 |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |

(56) References Cited

U.S. PATENT DOCUMENTS

| | | |
|---|---|---|
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |

(56) References Cited

U.S. PATENT DOCUMENTS

| | | |
|---|---|---|
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,616,431 B2 * | 12/2013 | Timm ............... A61B 17/072 227/178.1 |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 10,085,751 B2 * | 10/2018 | Overmyer ............ A61B 17/072 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 * | 3/2007 | Roby ............... A61B 17/1155 606/219 |
| 2009/0206130 A1 * | 8/2009 | Hall ............... A61B 17/07207 227/175.2 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 * | 3/2010 | Milliman ............ A61B 17/115 227/175.1 |

(56) References Cited

U.S. PATENT DOCUMENTS

| | | |
|---|---|---|
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0184459 A1* | 7/2011 | Malkowski ............ A61B 17/29 606/206 |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012289 A1* | 1/2014 | Snow ............ A61B 17/320016 606/130 |
| 2014/0012317 A1 | 1/2014 | Orban et al. |
| 2014/0135804 A1 | 5/2014 | Weisenburgh, II et al. |
| 2014/0373652 A1* | 12/2014 | Zergiebel ................ F16H 19/02 74/89.23 |
| 2015/0374366 A1* | 12/2015 | Zergiebel ............ A61B 17/068 74/89.23 |
| 2016/0106406 A1* | 4/2016 | Cabrera ............. A61B 17/1155 606/1 |
| 2016/0143641 A1 | 5/2016 | Sapienza et al. |
| 2016/0157856 A1 | 6/2016 | Williams et al. |
| 2016/0166255 A1* | 6/2016 | Fischvogt ............ A61B 17/068 606/139 |
| 2016/0174988 A1 | 6/2016 | D'Agostino et al. |
| 2016/0256184 A1* | 9/2016 | Shelton, IV ......... A61B 17/072 |
| 2016/0302792 A1 | 10/2016 | Motai |
| 2016/0310134 A1* | 10/2016 | Contini ............. A61B 17/0686 |
| 2018/0168575 A1* | 6/2018 | Simms ............... A61B 17/0682 |
| 2018/0168624 A1* | 6/2018 | Shelton, IV ..... A61B 17/07207 |
| 2018/0168627 A1* | 6/2018 | Weaner .................. A61B 34/30 |
| 2019/0357909 A1* | 11/2019 | Huitema ............ A61B 17/0682 |
| 2020/0046367 A1* | 2/2020 | Baril .................. A61B 17/1285 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2446835 A1 | 5/2012 |
| EP | 2524656 A2 | 11/2012 |
| EP | 3123960 A1 | 2/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

ROTATION ASSEMBLY FOR A SURGICAL DEVICE

CROSS-REFERENCE TO RELATED APPLICATIONS

This application claims the benefit of and priority to U.S. Provisional Patent Application No. 62/500,116 filed May 2, 2017, the entire disclosure of which is incorporated by reference herein.

BACKGROUND

1. Technical Field

The present disclosure is directed to a rotation assembly for supporting an adapter assembly on a handle assembly of a powered surgical device. More particularly, the present disclosure is directed to a rotation assembly for supporting an adapter assembly on a handle assembly of a powered surgical stapling device with an improved stop assembly for limiting a degree of rotation of the adapter assembly in relation to the handle assembly.

2. Background

Surgical devices, e.g., surgical stapling devices, include an actuator or handle assembly, an elongated body portion or adapter assembly, and a reload including a tool assembly. The adapter assembly is supported on and extends distally from the actuator assembly and the reload is supported on a distal portion of the adapter assembly.

In known surgical devices, the adapter assembly is rotatably supported in relation to the actuator assembly by a rotation assembly. The rotation assembly includes a rotatable knob that supports the adapter assembly and an inner housing that is fixedly secured to the actuator assembly. The rotatable knob is rotatable about the inner housing to facilitate rotation of the adapter assembly in relation to the actuator assembly, and thus, facilitate repositioning of the reload in relation to the actuator assembly.

In known electrically powered surgical stapling devices, the actuator assembly supports a power supply, e.g., a battery pack that supplies power to a motor within the actuator assembly to drive different assemblies of the stapling device, e.g., an approximation assembly, a firing assembly, and a knife assembly. In some devices, a wire harness is coupled between the actuator assembly and the reload to facilitate communication between a chip in the reload and a processor in the actuator assembly. The chip in the reload may be provided to identify the type and/or size of the reload and/or whether the reload has been previously fired. This information is sent via the wire harness to the processor in the actuator assembly to determine whether the actuator and the reload are compatible, and/or whether the reload has not been used. If the answer to any of these questions is no, the processor will deactivate the actuator assembly.

In such devices, the rotation assembly includes a stop member that limits the degree of rotation of the adapter assembly in relation to the actuator assembly to prevent uncoupling of the wire harness from the actuator assembly. In known devices, the stop member has a tendency to engage a flex cable of the wire harness as the adapter assembly is rotated in relation to the actuator assembly. This engagement sometimes results in damage to the flex cable which causes a loss in communication between the actuator assembly and the reload.

A continuing need exists for a surgical device having an improved rotation assembly to reduce the likelihood of damage to a wire harness extending between the actuator assembly and the reload of a surgical device during rotation of the adapter assembly in relation to the actuator assembly.

SUMMARY

One aspect of this disclosure is directed to a surgical device including an actuator assembly, an adapter assembly, and a tool assembly. The adapter assembly includes a rotation assembly and an elongated body portion. The tool assembly is supported on a distal portion of the elongated body portion. The rotation assembly includes an inner housing and a rotation knob. The inner housing defines a longitudinal axis and is releasably coupled to the actuator assembly. The rotation knob is rotatably supported about the inner housing and is coupled to the elongated body portion such that rotation of the rotation knob about the inner housing causes corresponding rotation of the elongated body portion about the longitudinal axis of the inner housing. The rotation knob supports a stop and the inner housing supports a stop member. The stop has first and second surfaces that are positioned to engage the stop member to limit a degree of rotation of the rotation knob in relation to the inner housing.

In some embodiments, the stop includes a stop plate that is C-shaped and includes first and second ends, the first end defining the first stop surface and the second end defining the second stop surface.

In embodiments, the stop member includes a stop pin.

In some embodiments, the stop plate is C-shaped and is configured to limit the degree of rotation of the rotation knob in relation to the inner housing to from about 90° to about 270°.

In certain embodiments, the stop plate is configured to limit the degree of rotation of the rotation knob in relation to the inner housing to 180°.

In embodiments, the tool assembly forms part of a reload assembly that is releasably coupled to the distal portion of the elongated body portion.

In some embodiments, the adapter assembly includes a wire harness having a proximal connector supported adjacent the actuator assembly and a distal connector supported adjacent the reload.

In certain embodiments, the wire harness includes a service loop that is supported partially about the inner housing proximally of the stop member.

In embodiments, the stop plate is formed from metal.

In some embodiments, the stop plate is fixedly received within a slot defined within the rotation knob.

In certain embodiments, the inner housing includes a cylindrical body defining an annular recess that is defined by a proximal wall and a distal wall that is spaced from the proximal wall, and the stop member and the stop plate are positioned within the annular recess.

In embodiments, the stop member extends distally from the proximal wall defining the annular recess.

In some embodiments, the tool assembly includes an anvil assembly and a shell assembly.

In certain embodiments, the shell assembly includes an annular staple cartridge.

Another aspect of the present disclosure is directed to an adapter assembly including an elongated body portion and a rotation assembly supported on a proximal portion of the elongated body portion. The rotation assembly includes an inner housing defining a longitudinal axis and a rotation knob. The rotation knob is supported on the inner housing and is rotatable about the longitudinal axis of the inner housing. The elongated body portion is supported on the rotation knob such that rotation of the rotation knob about the inner housing causes corresponding rotation of the elongated body portion about the longitudinal axis. The rotation knob supports a stop plate and the inner housing supports a stop member. The stop plate has first and second ends that are positioned to engage the stop member to limit a degree of rotation of the rotation knob in relation to the inner housing about the longitudinal axis.

BRIEF DESCRIPTION OF THE DRAWINGS

Various embodiments of a surgical stapling device including a rotatable adapter assembly with the presently disclosed rotation assembly are described herein below with reference to the drawings, wherein.

DETAILED DESCRIPTION OF EMBODIMENTS

The presently disclosed rotation assembly will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through a small diameter incision or cannula. In addition, the term clinician is used generally to refer to medical personnel including doctors, nurses, and support personnel.

The presently disclosed rotation assembly forms part of a surgical device that includes an actuator assembly including a handle, an adapter assembly extending distally from the actuator assembly, and a tool or reload assembly supported on a distal portion of the adapter assembly. The rotation assembly forms part of the adapter assembly and rotatably supports the adapter assembly in relation to the actuator assembly. The adapter assembly includes a wire harness that extends between the actuator assembly and the reload assembly to facilitate communication between the actuator assembly and the reload assembly. The rotation assembly includes a stop assembly for limiting a degree of rotation of the adapter assembly in relation to the actuator assembly to prevent separation of the wire harness from the actuator assembly and/or the reload assembly. The stop assembly includes a stop member that is spaced from the wire harness a sufficient distance to minimize the likelihood of damage to the wire harness during rotation of the adapter assembly in relation to the actuator assembly. Although the present disclosure is directed to a circular stapling device, it is envisioned that the presently disclosed rotation assembly including the stop assembly could be incorporated into a variety of different devices including linear stapling devices, ligation devices, clip appliers, and vessel sealing devices.

Figure 1:
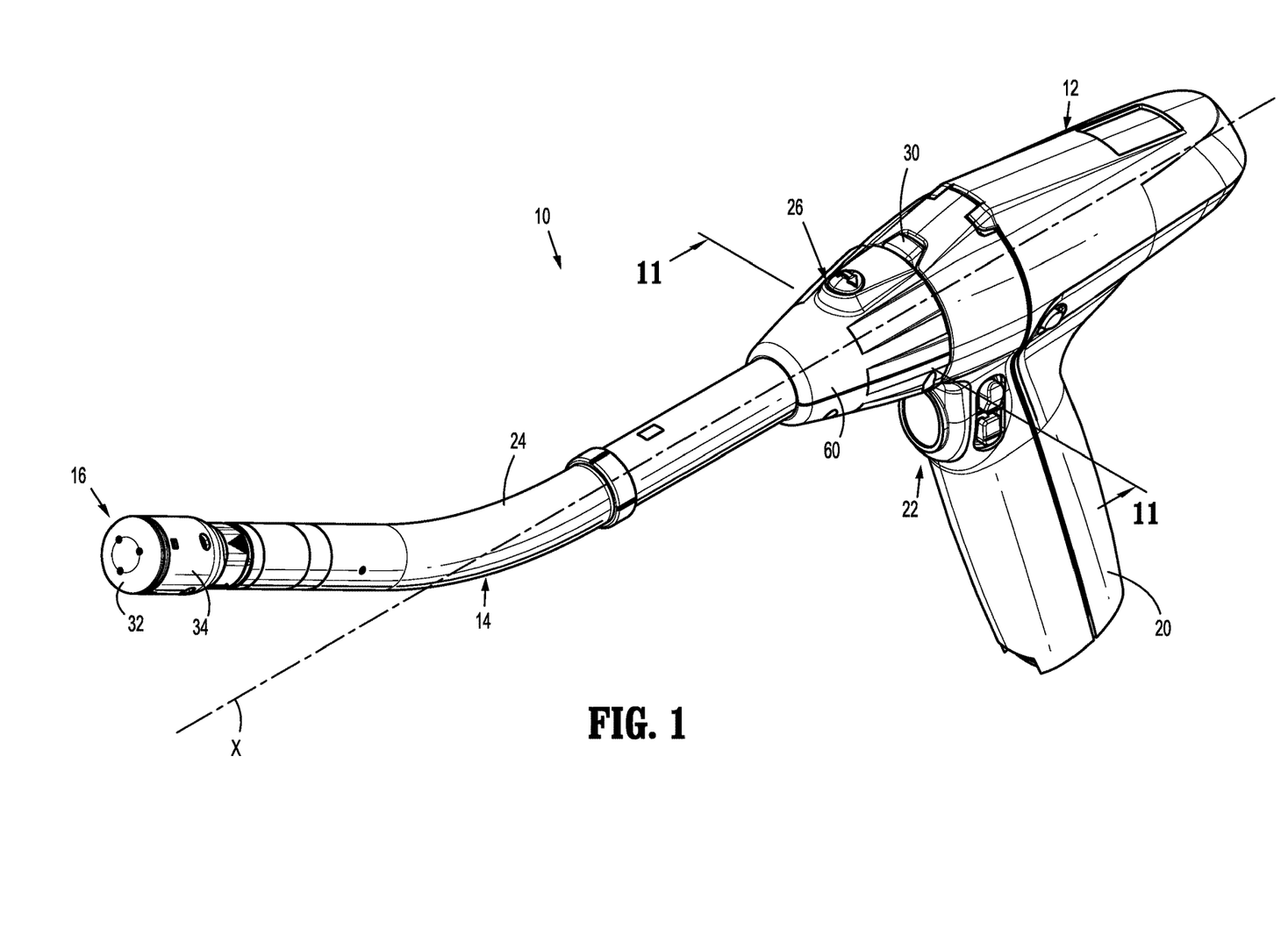
FIG. 1 is a side perspective view of a powered surgical stapling device including an exemplary embodiment of the presently disclosed rotation assembly with an adapter assembly of the powered surgical stapling device positioned in a first orientation in relation to an actuator assembly of the powered surgical stapling device.
Figure 2:
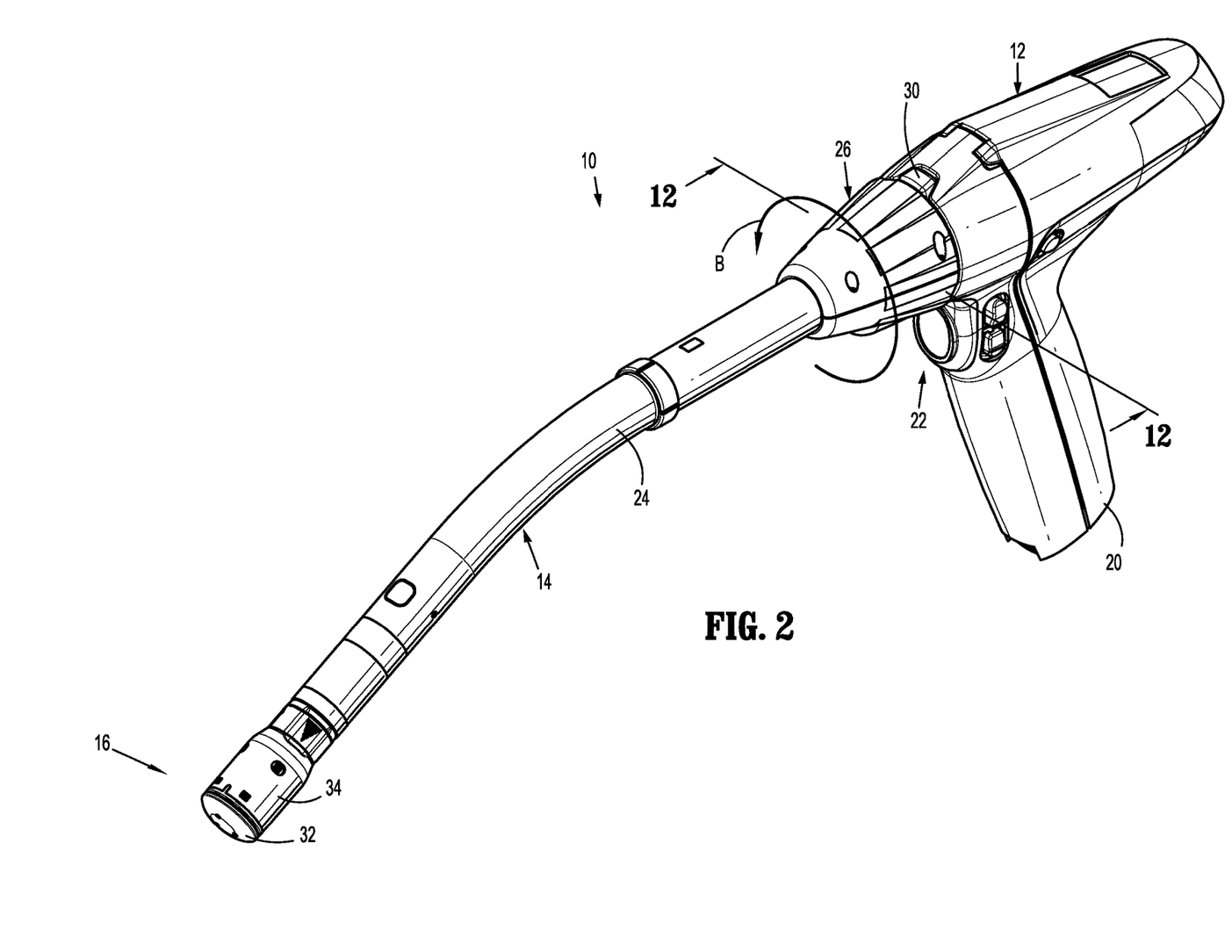
FIG. 2 is a side perspective view of the powered surgical stapling device shown in FIG. 1 with the adapter assembly rotated to a second orientation in relation to the actuator assembly.

Referring to FIGS. 1 and 2, a surgical stapling device 10 includes an actuator assembly 12, an adapter assembly 14, and a reload assembly 16. The adapter assembly 14 has a proximal portion that is releasably coupled to the actuator assembly 12, and a distal portion that is releasably coupled to the reload assembly 16. The surgical stapling device 10 is an electromechanically powered system such as disclosed in U.S. Patent Publication Nos. 2015/0108201, 2015/0048140, and 2015/0076206 which are incorporated herein by reference in their entirety. The actuator assembly 12 includes a stationary handle 20 and a plurality of actuation buttons 22 that control different functions of the stapling device 10, e.g., approximation, stapling, and cutting. In embodiments, the stationary handle 20 supports a battery pack (not shown) for powering the actuator assembly 12 and a processor (not shown) for controlling operation of the actuator assembly 12.

Figures 3, 4:
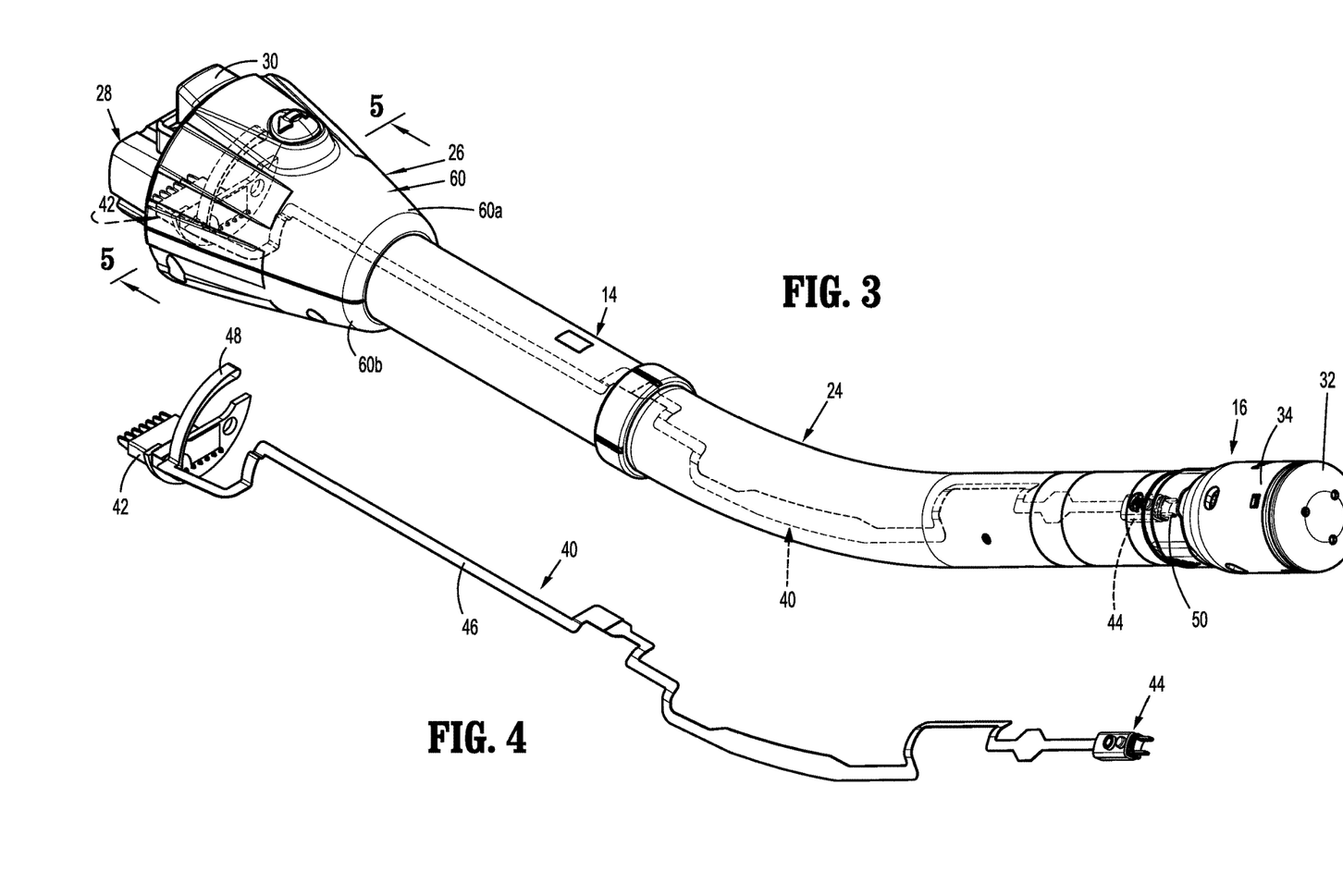
FIG. 3 is a side perspective view of the adapter assembly of the powered surgical stapling device shown in FIG. 1 with a wire harness of the adapter assembly shown in phantom.
FIG. 4 is a side perspective view of the wire harness of the adapter assembly shown in FIG. 3.

Referring to FIG. 3, the adapter assembly 14 is positioned between the actuator assembly 12 and the reload assembly 16 to translate power from the actuator assembly 12 to the reload assembly 16. The adapter assembly 14 includes an elongated body 24, a rotation assembly 26, and a coupling assembly 28 (FIG. 3). The coupling assembly 28 includes a release button 30 that can be depressed to uncouple the adapter assembly 26 from the actuator assembly 12. The rotation assembly 26 supports the elongated body 24 of the adapter assembly 14 in relation to the actuator assembly 12 about a longitudinal axis "X" (FIG. 1) of the rotation assembly 26 and is described in further detail below.

In the illustrated embodiment, the reload assembly 16 includes a circular stapler including an anvil assembly 32 and a shell assembly 34. In embodiments, the shell assembly 34 is releasably coupled to the distal portion of the elongated body 24. U.S. Patent Publication Nos. 2016/0192938, 2016/0192934, and 2016/0310141 disclose exemplary embodiments of a circular stapler that is releasably coupled to an adaptor assembly and are incorporated herein by reference in their entirety.

Referring also to FIG. 4, the adapter assembly 14 includes a wire harness 40 that includes a proximal connector 42, a distal connector 44, a flex cable 46, and a service loop 48. The proximal connector 42 is connected to the actuator assembly 12 and the distal connector 44 is connected to the reload assembly 16. In embodiments, the actuator assembly 12 includes a processor (not shown) and the reload assembly 16 includes a chip 50. The wire harness 40 provides a path of communication between the processor (not shown) and the chip 50 to allow information stored in the chip 50 to be sent to the processor. In embodiments, the chip 50 includes information such as the type of the reload 16, the size of the reload, and/or the status of the reload, e.g., fired or unfired.

As discussed above, the elongated body 24 of the adapter assembly 14 is supported by the rotation assembly 26 such that the elongated body 24 and the reload assembly 16 are rotatable in relation to the actuator assembly 12 about the longitudinal axis "X" (FIG. 1). As such, when the elongated body 24 is rotated about the longitudinal axis "X", the distal connector 44 which is secured to the reload 16 rotates in relation to the proximal connector 42 which is secured to the handle assembly 12 (FIG. 1). The service loop 48 includes an overlapping portion of flex cable 46 which is fed out as the connectors 42 and 44 become further spaced to allow for some degree of relative rotation between the proximal and distal connectors 42, 44 to occur without the proximal and/or distal connectors 42, 44 becoming separated from the actuator assembly 12 and reload assembly 16, respectively.

Figure 8:
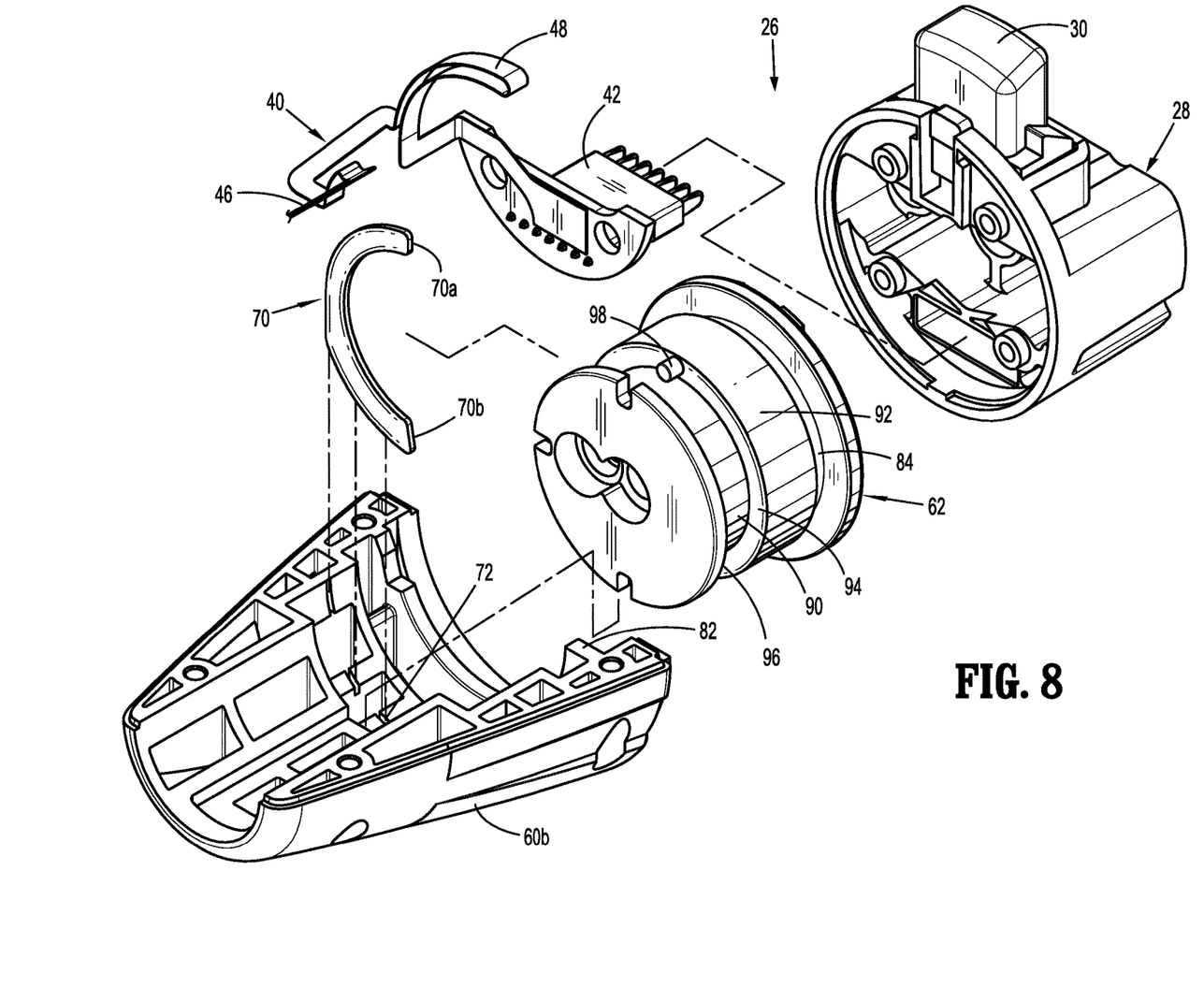
FIG. 8 is a side perspective exploded view of the rotation assembly of the powered surgical stapling device shown in FIG. 1 and a proximal portion of the wire harness.

The rotation assembly 26 includes an outer rotation knob 60 and an inner housing 62 (FIG. 8). In embodiments, the outer rotation knob 60 is formed from molded half-sections 60a, 60b and is rotatably supported about the inner housing 62. The outer rotation knob 60 supports the elongated body 24 such that rotation of the outer rotation knob 60 about the inner housing 62 causes rotation of the elongated body 24 in relation to the actuator assembly 12 about the longitudinal axis 12 (FIG. 1). In order to prevent over-rotation of the elongated body portion 24 of the adapter assembly 14 in relation to the actuator assembly 12, the rotation assembly 26 is provided with a rotation stop assembly described in detail below.

Figure 5:
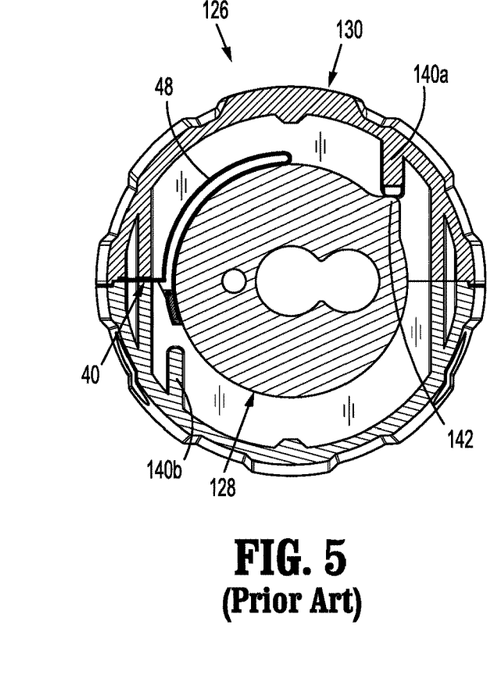
FIG. 5 is a cross-sectional view taken along section line 5-5 of the adapter assembly of FIG. 3 illustrating a Prior Art rotation assembly with internal components of the adapter assembly removed.
Figure 6:
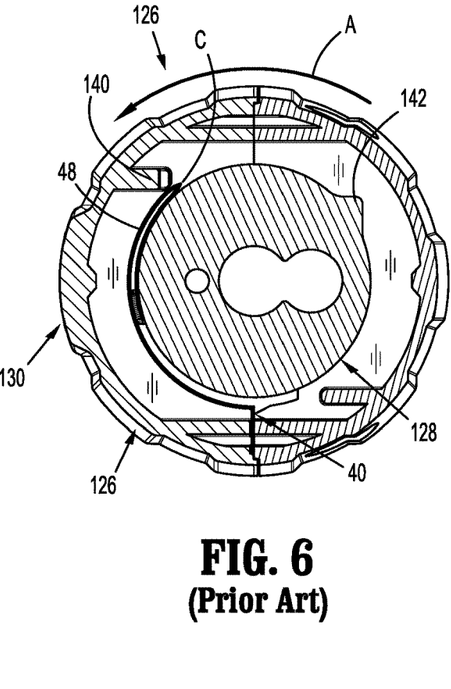
FIG. 6 is a cross-sectional view as shown in FIG. 5 of the Prior Art rotation assembly of the adapter assembly as an outer knob housing of the rotation assembly is rotated in a counter clockwise direction about an inner housing of the rotation assembly with a service loop of the wire harness engaged with a stop member of the rotation assembly.
Figure 7:
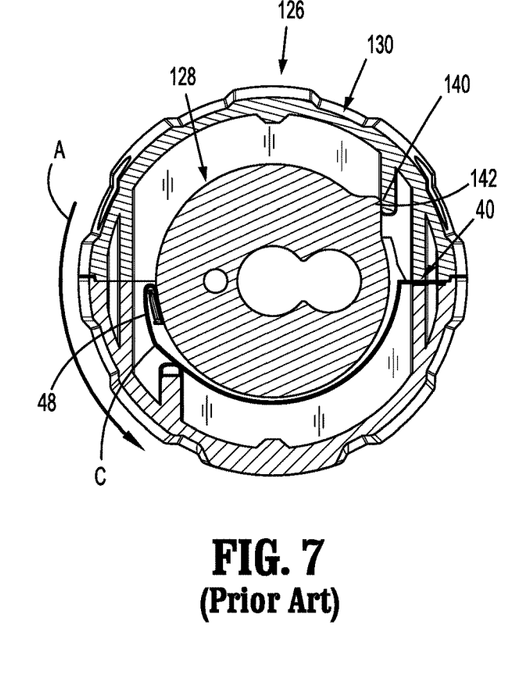
FIG. 7 is a cross-sectional view as shown in FIG. 5 of the Prior Art rotation assembly of the adapter assembly as an outer knob housing of the rotation assembly is rotated further about the inner housing of the rotation assembly in the counter-clockwise direction with a crease formed in the service loop of the wire harness.

FIGS. 5-7 illustrate a prior art rotation assembly 126 including an inner housing 128 and a rotation knob 130. As discussed above with regard to the rotation assembly 26, the rotation knob 130 is rotatably supported about the inner housing 128 to effect rotation of an elongated body (not shown) of an adapter assembly (not shown) in relation to an actuator assembly (not shown). As shown, the service loop 48 of the wire harness 40 is sized to allow rotation of the rotation knob 126 about the inner housing 128 over an arc of about 180° degrees. In order to prevent over-rotation of the rotation knob 130 in relation to the inner housing 128, the rotation assembly 126 includes a stop assembly including first and second stop ribs 140a, 140b, respectively that extend inwardly from the rotation knob 130, and a stop protrusion 142 that extends outwardly from the inner housing 128. As shown, the stop ribs 140a, 140b are spaced within the rotation about 180 degrees apart to allow the rotation knob 130 to rotate about the inner housing 128 over an arc of about 180 degrees. As the rotation knob 130 rotates about the inner housing 128 in the direction indicated by arrow "A" in FIGS. 6 and 7, the stop rib 140a moves from a position engaged with one side of the stop protrusion 142 to a position spaced about 180 degrees from the stop protrusion 142. Similarly, the stop rib 140b moves from a position spaced about 180 degrees from the other side of the stop protrusion 142 into engagement with the stop protrusion 142 to prevent further rotation of the rotation knob 126 in direction "A". As the rotation knob 130 is rotated about the inner housing 128, the stop rib 140a engages and compresses the service loop 50 of the wire harness 40 against the inner housing 128. The engagement between the stop rib 140a and the service loop 50 of the wire harness 40 has a tendency to form a crease "C" (FIG. 7) in the wire harness 40. This crease "C" may result in a loss in communication between the actuator assembly 14 and the reload 16 (FIG. 1).

Figure 9:
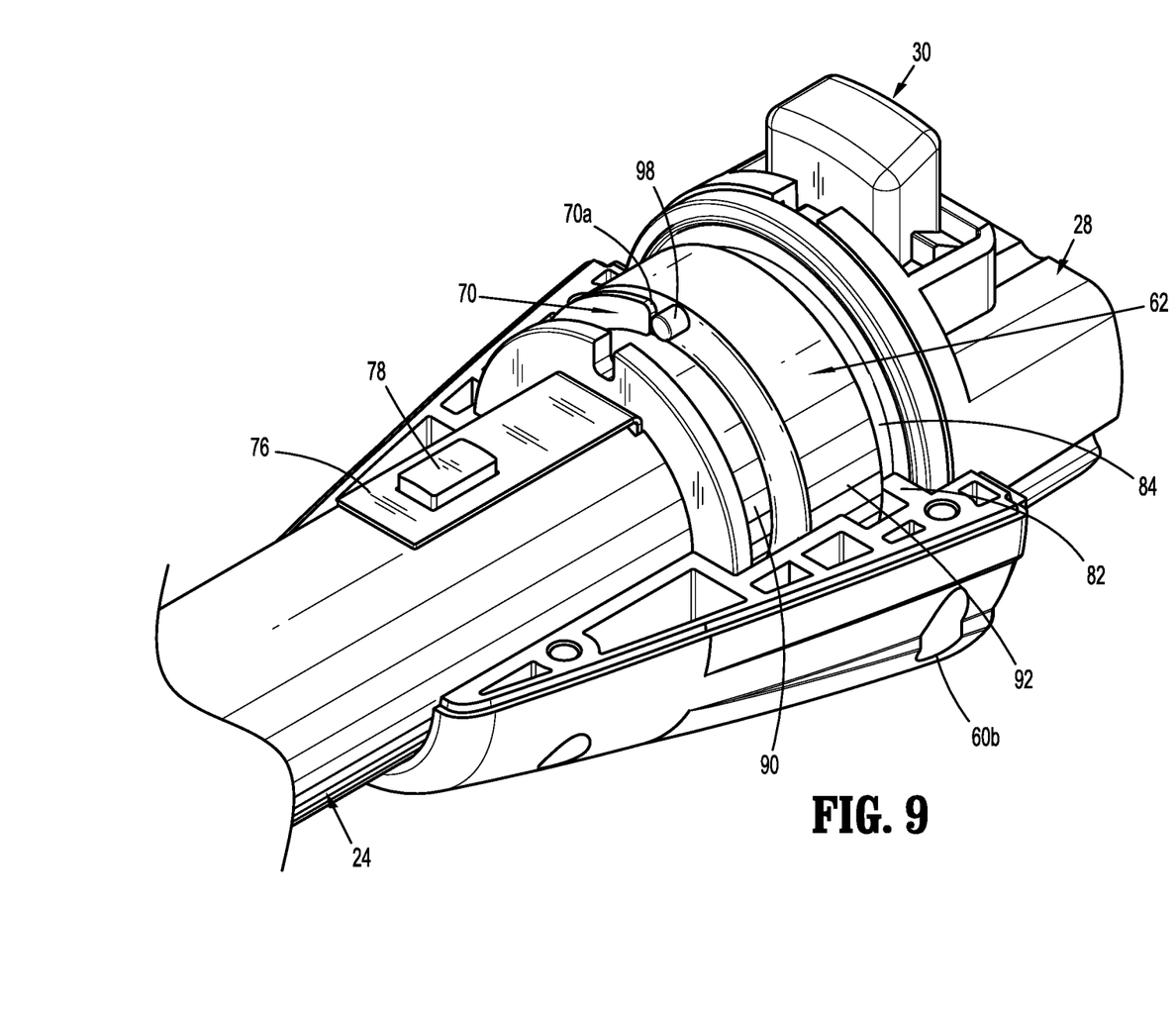
FIG. 9 is a side perspective view of a proximal portion of the adapter assembly shown in FIG. 3 including the rotation assembly with a half-section of the rotation knob removed from a first side of the adapter assembly.
Figure 9A:
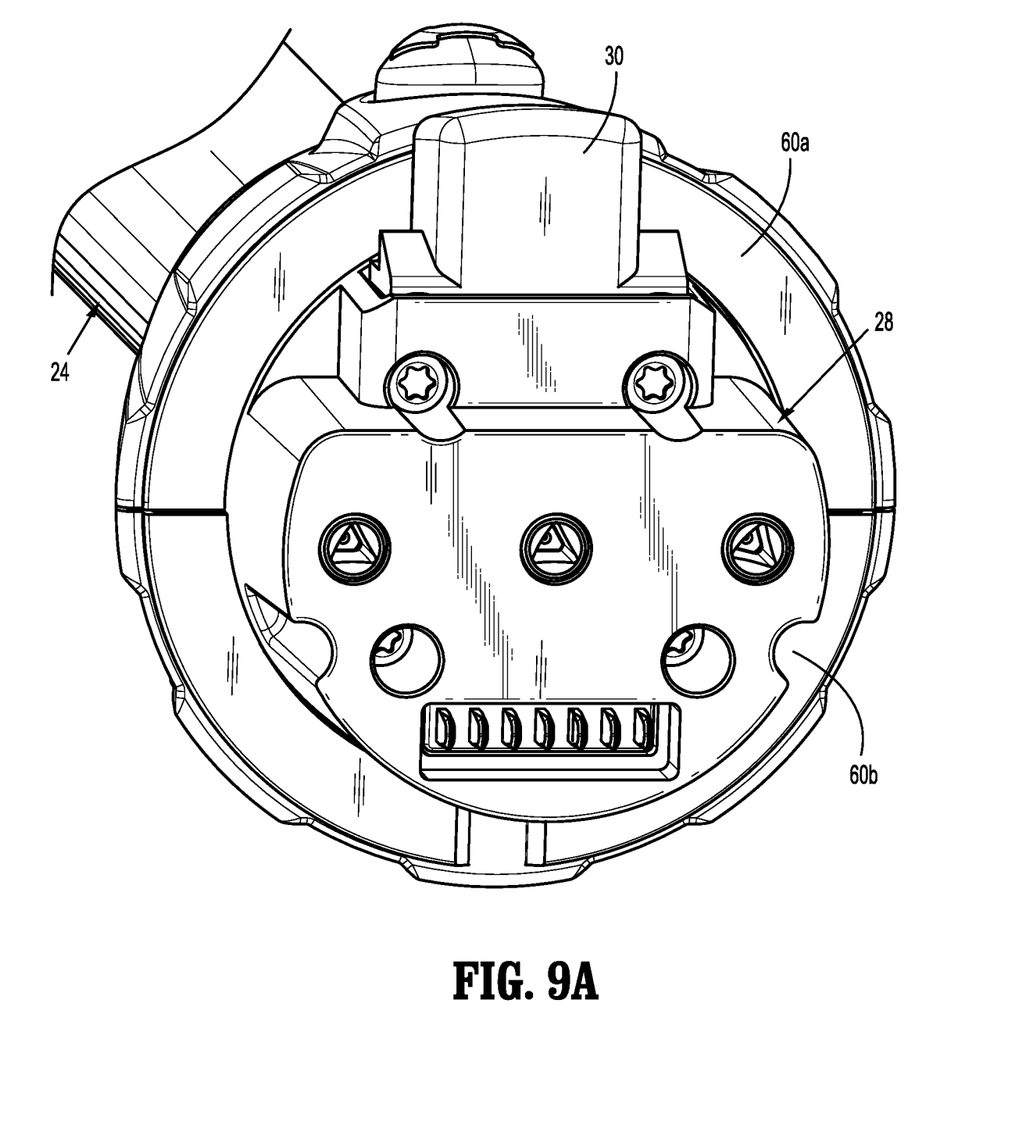
FIG. 9A is a rear end view of the adapter assembly shown in FIG. 3.
Figure 10:
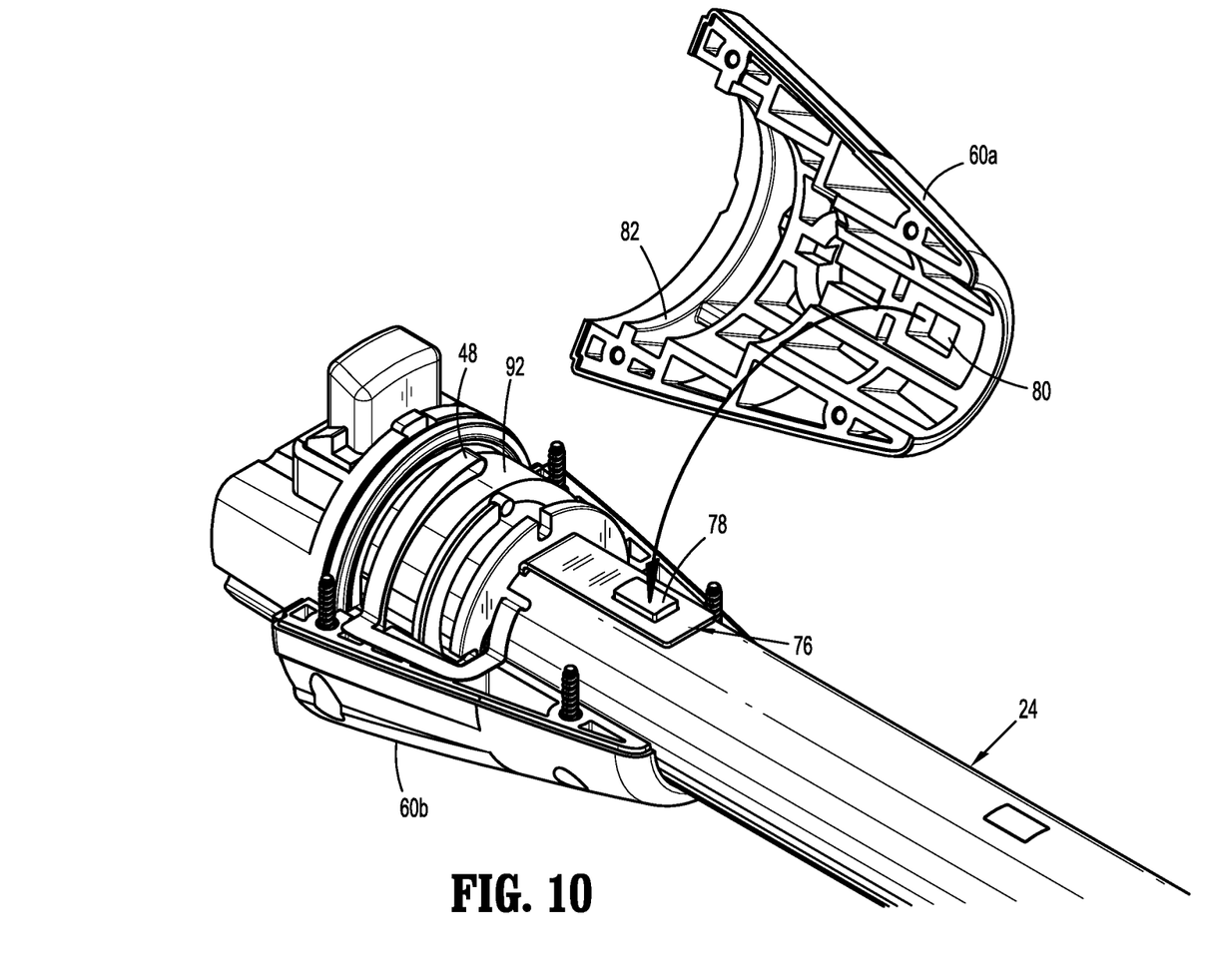
FIG. 10 is a side perspective view of a proximal portion of the adapter assembly shown in FIG. 3 including the rotation assembly with a first half-section of the rotation knob of the rotation assembly separated from a second half-section of the rotation.
Figure 11:
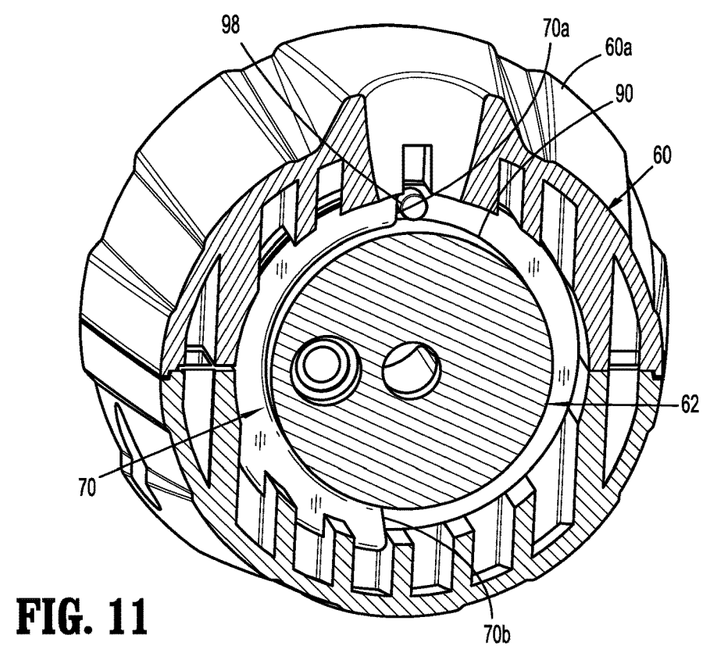
FIG. 11 is a cross-sectional view taken along section line 11-11 of FIG. 1 with the rotation knob positioned in a first orientation.
Figure 12:
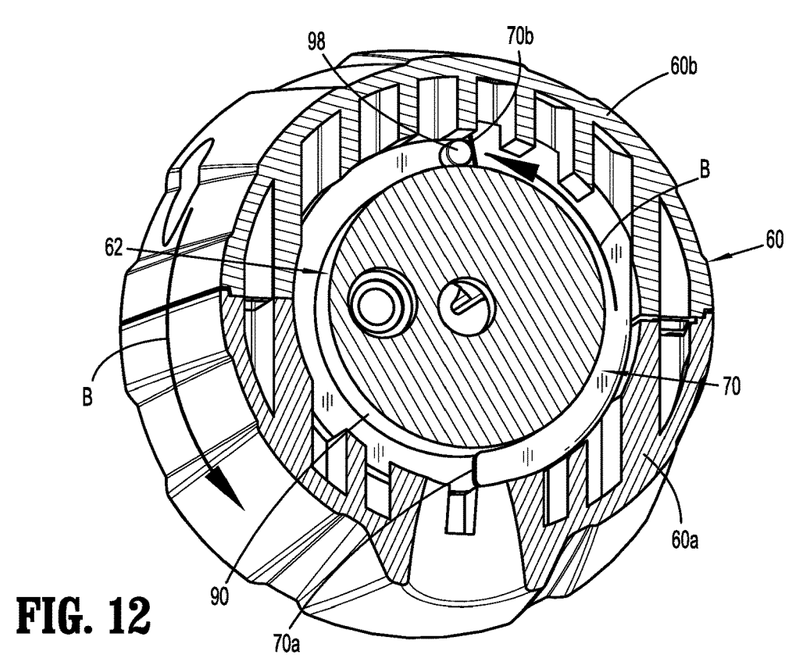
FIG. 12 is a cross-sectional view taken along section line 11-11 of FIG. 1 with the rotation knob positioned in a second orientation.

Referring to FIGS. 8-10, in the presently disclosed rotation assembly 26, the rotation knob 60 supports a stop 70 having first and second stop surfaces 70a, 70b. In embodiments, the stop 70 is formed from a plate having an annular configuration that is received within an annular slot 72 formed in the half-sections 60a and 60b of the rotation knob 60 such as by press-fitting. Alternately, the stop 70 can assume a variety of configurations and be attached to the rotation knob 60 using a variety of known other attachment methods. In embodiments, the stop plate 70 has first and second ends that define the stop surfaces 70a and 70b. In some embodiments, the stop plate 70 is substantially C-shaped and extends over an arc of from about 90 degrees to about 270 degrees. In other embodiments, the stop plate 70 extends over an arc of about 180 degrees.

The elongated body 24 of the adapter assembly 14 supports a clip 76 that defines a protrusion 78. The protrusion 78 is received within a recess 80 (FIG. 10) defined within the half-section 60a of the rotation knob 60 to rotatably fix the rotation knob 60 to the elongated body 24 of the adapter assembly 14.

Each of the half-sections 60a, 60b of the rotation knob 60 includes an annular flange 82. The inner housing 62 of the rotation assembly 26 includes an annular slot 84 that receives the annular flange 82 to rotatably secure the rotation knob 60 about the inner housing 62.

The inner housing 62 of the rotation assembly 26 defines an annular recess 90 and an annular race 92. The annular recess 90 is positioned to receive the stop plate 70 and is defined by a proximal wall 94 (FIG. 8) and a distal wall 96 that is spaced from the proximal wall 94. The annular race 92 is positioned proximally of the annular recess 90 and defines a smooth cylindrical surface that is positioned to slidably engage the service loop 48 of the wire harness 40. A stop member 98 is supported on the inner housing 62 of the rotation assembly 26 within the annular recess 90. In embodiments, the stop member 98 includes a stop pin that extends distally from the proximal wall 94 defining the annular recess 90. Alternately, the stop member 98 may have a variety of different configurations such that the stop member 98 interacts with the stop surfaces 70a, 70b of the stop plate 70 to limit the degree of rotation of the rotation knob 60 about the inner housing 62 of the rotation assembly 26.

Referring to FIGS. 1, 2, 11 and 12, the rotation knob 60 of the surgical stapling device 10 (FIG. 1) is rotatable about the inner housing 62 (FIG. 11) of the rotation assembly 26 to change the orientation of the reload assembly 16 in relation to the actuator assembly 12 (FIG. 1) from that shown in FIG. 1 to that shown in FIG. 2. In the orientation shown in FIG. 1, a first side of the stop member 98 is positioned in abutment with the stop surface 70a (FIG. 11) of the stop plate 70. When the rotation knob 60 is rotated about the inner housing 62 of the rotation assembly 26 in the direction indicated by arrow "B" in FIGS. 2 and 12, the stop surface 70a of the stop member 70, which is supported on the rotation knob 60, rotates away from the stop member 98 of the inner housing 62 and the stop surface 70b is rotates towards the opposite side of the stop member 98. When the stop surface 70b engages the stop member 98 (FIG. 12), further rotation of the rotation knob 60 about the inner housing 62 is prevented. As illustrated, engagement between the stop surfaces 70a, 70b and the stop member 98 takes place within the annular recess 90 (FIG. 9) of the inner housing at a location spaced distally of the service loop 48 of the wire harness 40. As discussed above, the service loop 48 of the wire harness 40 is supported on the cylindrical race 92 of the inner housing 62 of the rotation assembly 26 spaced from the stop plate 70 to prevent crimping of the service loop 48 during rotation of the adapter assembly 14 and reload 16 in relation to the actuator assembly 12 of the surgical stapling device 10.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical device comprising:
an actuator assembly;
an adapter assembly including a rotation assembly and an elongated body portion, the rotation assembly including an inner housing and a rotation knob, the inner housing defining a longitudinal axis and being releasably coupled to the actuator assembly, the rotation knob being rotatably supported about the inner housing and the elongated body portion being supported on the rotation knob such that rotation of the rotation knob about the inner housing causes corresponding rotation of the elongated body portion about the longitudinal axis of the inner housing; and
a tool assembly supported on a distal portion of the elongated body portion;
wherein the rotation knob supports a stop plate and the inner housing supports a stop member, the stop plate having first and second ends, each of the first and second ends of the stop plate being positioned to engage the stop member to limit a degree of rotation of the rotation knob in relation to the inner housing about the longitudinal axis.

2. The surgical device of claim 1, wherein the stop plate is C-shaped and the first end defines a first stop surface and the second end defines a second stop surface.

3. The surgical device of claim 2, wherein the stop plate is configured to limit the degree of rotation of the rotation knob in relation to the inner housing to from 90° to 270°.

4. The surgical device of claim 3, wherein the stop plate is configured to limit the degree of rotation of the rotation knob in relation to the inner housing to 180°.

5. The surgical device of claim 4, wherein the adapter assembly includes a wire harness having a proximal connector supported adjacent the actuator assembly and a distal connector supported adjacent the reload.

6. The surgical device of claim 5, wherein the wire harness includes a service loop, the service loop being supported partially about the inner housing at a location proximally of the stop member.

7. The surgical device of claim 2, wherein the stop plate is formed from metal.

8. The surgical device of claim 2, wherein the stop plate is fixedly received within a slot defined within the rotation knob.

9. The surgical device of claim 2, wherein the inner housing includes a cylindrical body defining an annular recess, the annular recess being defined by a proximal wall and a distal wall that is spaced from the proximal wall, the stop member and the stop plate being positioned within the annular recess.

10. The surgical device of claim 9, wherein the stop member extends distally from the proximal wall defining the annular recess.

11. The surgical device of claim 1, wherein the tool assembly forms part of a reload assembly, the reload assembly being releasably coupled to the distal portion of the elongated body portion.

12. The surgical device of claim 1, wherein the tool assembly includes an anvil assembly and a shell assembly.

13. The surgical device of claim 12, wherein the shell assembly includes an annular staple cartridge.

14. An adapter assembly comprising:
a rotation assembly including an inner housing and a rotation knob, the inner housing defining a longitudinal axis and the rotation knob being rotatably supported on the inner housing about the longitudinal axis; and
an elongated body portion supported on the rotation knob such that rotation of the rotation knob about the inner housing causes corresponding rotation of the elongated body portion about the longitudinal axis;
wherein the rotation knob supports a stop plate and the inner housing supports a stop member, the stop plate having first and second ends, each of the first and second ends of the stop plate being positioned to engage the stop member to limit a degree of rotation of the rotation knob in relation to the inner housing about the longitudinal axis.

15. The adapter assembly of claim 14, wherein the stop plate is C-shaped and limits the degree of rotation of the rotation knob in relation to the inner housing to from 90° to 270°.

16. The adapter assembly of claim 14, wherein the adapter assembly includes a wire harness having a first plug supported adjacent a distal end of the elongated body portion and a second plug supported adjacent a proximal end of the elongated body portion.

17. The adapter assembly of claim 16, wherein the wire harness includes a service loop supported partially about the inner housing, the service loop being positioned proximally of the stop member.

18. The adapter assembly of claim 14, wherein the stop plate is fixedly received within a slot defined within the rotation knob.

19. The adapter assembly of claim 14, wherein the inner housing includes a cylindrical body defining an annular recess defined by a proximal wall and a distal wall, the stop member and the stop plate being positioned within the annular recess.

20. The adapter assembly of claim 19, wherein the stop member extends distally from the proximal wall defining the annular recess.

* * * * *